United States Patent

Nevel et al.

[11] Patent Number: 5,875,419
[45] Date of Patent: Feb. 23, 1999

[54] SYSTEM AND METHOD FOR DETERMINING YARN HAIRINESS

[75] Inventors: Avishai Nevel, Providence; Kendall W. Gordon, Jr., North Kingston, both of R.I.; Steven Leary, Berkley, Mass.

[73] Assignee: Lawson-Hemphill, Inc.

[21] Appl. No.: 557,965

[22] Filed: Nov. 13, 1995

[51] Int. Cl.[6] .................................................... G01N 21/00
[52] U.S. Cl. .................... 702/157; 702/155; 364/470.14; 364/470.15; 356/384; 250/559.01; 250/559.12; 250/559.19
[58] Field of Search ................................ 364/563, 470.14, 364/470.15, 528.38; 356/336, 376, 381, 382, 384, 385, 386, 387, 430, 429, 431, 237, 238; 348/88, 91, 92, 93; 19/0.23; 57/264, 265; 73/159, 160; 250/559.24, 559.01, 559.04, 559.05, 559.06, 559.07, 559.08, 559.12, 559.15, 559.19, 559.22, 559.27, 559.28; 702/33, 34, 35, 49, 97, 128, 134, 137, 155, 157, 170, 172

[56] References Cited

U.S. PATENT DOCUMENTS

| 4,887,155 | 12/1989 | Massen .................................. 358/107 |
| 5,319,578 | 6/1994 | Lawson et al. ........................ 364/563 |
| 5,570,188 | 10/1996 | Nevel et al. ........................... 356/385 |

FOREIGN PATENT DOCUMENTS

578975A1  1/1994  European Pat. Off. .

Primary Examiner—Emanuel Todd Voeltz
Assistant Examiner—Hal P. Wachsman
Attorney, Agent, or Firm—Brian M. Dingman

[57] ABSTRACT

A computer-controlled device for determining relative yarn hairiness. Yarn is moved past a light source to create a yarn shadow, and an imaging device captures the yarn shadow. The imaging device includes a number of separate, closely-spaced light sensing elements, each with an output level related to the amount of light shining on the element. A selected sensing element output level is established as indicative that an element is blocked by the yarn. The width of a number of closely-spaced portions of the yarn is determined, at two different selected sensing elements output levels, to distinguish the yarn hairs from the yarn core.

10 Claims, 5 Drawing Sheets

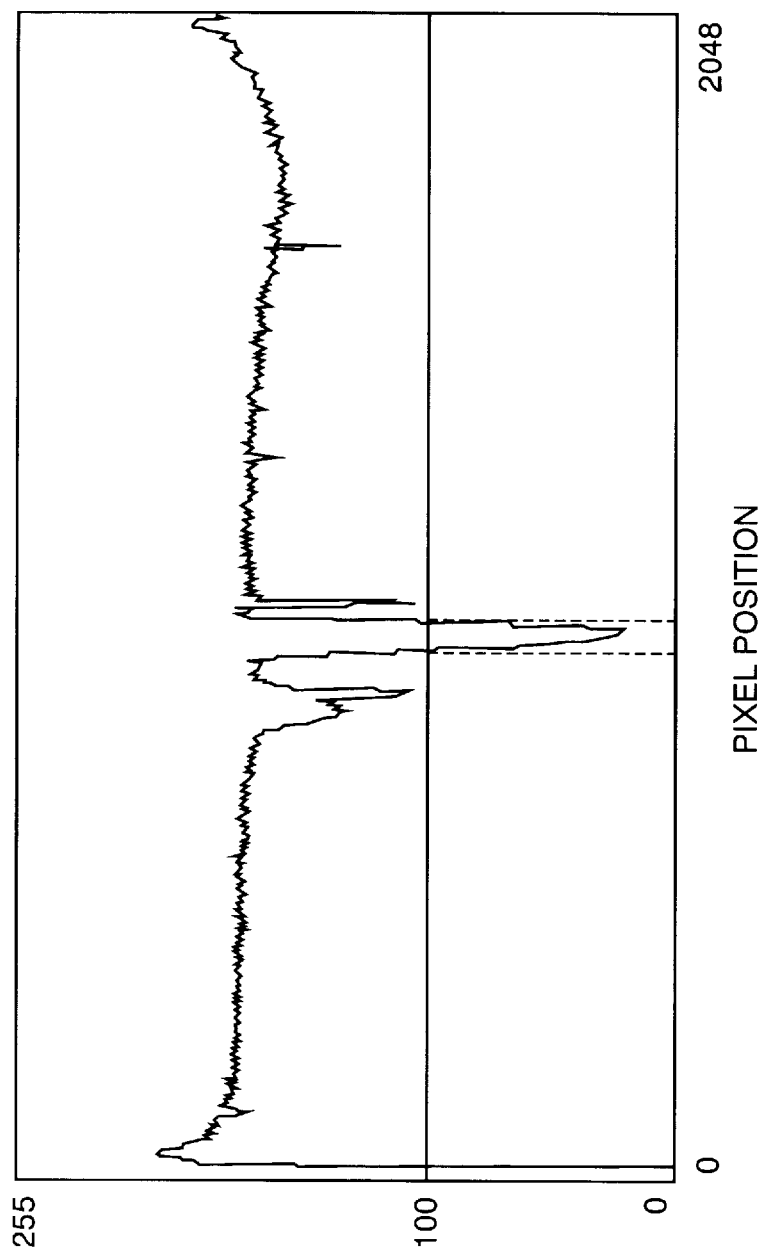

SYSTEM AND METHOD FOR DETERMINING YARN HAIRINESS

FIELD OF INVENTION

This invention relates to a system and method for determining yarn hairiness by comparing images of the yarn under test.

BACKGROUND OF INVENTION

Many yarns, particularly spun yarns, consist of a central core of relatively tightly-intermeshed fibers, surrounded by a region of progressively less-dense fibers protruding from the core. The protruding fibers are termed yarn hairiness. The amount of hairiness is important to both textile operations as well as fabric appearance. In operations such as air jet weaving, the aerodynamics of the yarn influence the amount of energy necessary to move the yarn. The amount of hairiness also contributes to the quality of the yarn, and the final appearance of fabric made from the yarn. Thus, knowledge of yarn hairiness is important.

One of the current methods used to measure yarn hairiness is embodied in the Zweigle hairiness tester. The Zweigle tester has a lamp which shines a light only on yarn fibers which protrude above the yarn core. The fiber images are projected onto twelve photo transistors, each of which is a different height from the bottom of the yarn core. The number of fibers projecting to each of the twelve heights is counted. A problem with this approach is that the device does not account for or measure the yarn core. Also, the actual length of fibers must be measured outward from the periphery of the yarn core. However, since Zweigle tester does not determine the core thickness, the actual fiber lengths are not measured.

The second basic method of yarn testing is embodied in the Uster Tester 3. This device shines light on the yarn. The device has an aperture in front of the detector whose purpose is to block any light that would move directly from the light source to the receiver. The optical receiver, then, picks up only light that is scattered by the yarn. The detector transforms the light received into proportional electrical signals for evaluation. This system, however, directly measures only the light-scattering properties of yarn—there is no direct measurement of hairiness. Any factors which could affect the light scattering capability of the yarn, including the density of the core, the thickness of the fibers, and the fiber reflectivity, would all contribute to the measured value, despite the fact that these factors do not contribute to hairiness. Accordingly, this test is qualitative. Clearly, the test does not result in the actual determination of hairiness, the length of the hairs, or the diameter of the yarn core.

SUMMARY OF THE INVENTION

It is therefore an object of this invention to provide a method and system for directly determining yarn hairiness.

It is a further object of this invention to provide such a method and system that is able to separate the core of the yarn from the yarn hairiness.

This invention features in one embodiment a method of determining yarn hairiness, comprising: measuring the diameter of the yarn as including at least some hairs; measuring the diameter of the yarn as including fewer hairs; and comparing the measured diameters to determine the overall yarn hairiness.

The diameter measurement steps may be yarn shadow measurement steps that may be accomplished by shining a light on the yarn and capturing an image of the yarn shadow. The image may be captured with an imaging device with an output level related to the amount of light shining on the device. This imaging device may include a number of separate, closely-spaced light sensing elements, each with an output level, for example a charge-coupled device (CCD). The yarn shadow measurements may include first establishing the sensing element output level indicative of an element being blocked by the yarn from receiving sufficient light. The yarn diameter may be established by determining the furthest-spaced pair of light sensing elements that are blocked by the yarn at the established sensing element output level. Relative hairiness may be determined by making such measurements on the yarn with a relatively large sensing element output level as indicative that the element is blocked by the yarn, to make the sensing elements more sensitive to yarn hairs, and also by measuring the core of the yarn by establishing a relatively low sensing element output level and then making the measurements. An indicator of yarn hairiness may then be determined by dividing the overall diameter by the core diameter.

In another embodiment this invention features a computer program residing in the memory of a computer that is responsive to a yarn profile analyzer device, in which the yarn profile analyzer device includes a light source for shining light on a moving yarn, and an imaging device capturing a shadow image of the moving yarn, the imaging device including a number of separate, closely-spaced light sensing elements, each with an output level related to the amount of light shining on the element. The computer program includes means for establishing a relatively large sensing element output level as indicative that an element is blocked by the yarn, to make the sensing elements more sensitive to yarn hairs; and computer program means for establishing a relatively low sensing element output level as indicative that an element is blocked by the yarn, to make the sensing element less sensitive to yarn hairs, for measuring the yarn core, to assist in distinguishing the yarn hairs from the yarn core.

In yet another embodiment this invention features a computer-controlled device for determining relative yarn hairiness, comprising: a light source; means for moving yarn past the light source to create a yarn shadow; an imaging device for capturing the yarn shadow, and including a number of separate, closely-spaced light sensing elements, each with an output level related to the amount of light shining on the element; means for establishing a selected sensing element output level as indicative that an element is blocked by the yarn; and means for determining and capturing the yarn width of a number of closely-spaced portions of the yarn, the width established by the furthest-spaced pair of blocked sensing elements, at two different selected sensing elements output levels, to distinguish the yarn hairs from the yarn core.

BRIEF DESCRIPTION OF THE DRAWINGS

Other objects, features and advantages will occur to those skilled in the art from the following description of the preferred embodiments, and the accompanying drawings, in which:

FIGS. 2A, 2B and 2C are exemplary graphs of a single scan of the camera of FIG. 1 with three different light level thresholds, useful in understanding this invention.

DESCRIPTION OF THE PREFERRED EMBODIMENTS

Hairiness measurement to date has been problematic. Even devices that directly measure hairs do not measure the yarn core, or account for the core diameter in making hairiness measurements—they simply measure the distance from the bottom of the core to the ends of the fibers. Thus, the determined fiber length actually includes the core diameter.

This invention accomplishes two measurements of a yarn, one measurement of the diameter of the yarn including at least some of the yarn hairs, and a second measurement of the diameter including fewer hairs. The measurements are preferably made with a measuring device that has a hairiness density sensitivity adjustability to allow few of, or most of, the hairs to be blocked from the measurements in order to separate the core from the hairs.

Figure 1:
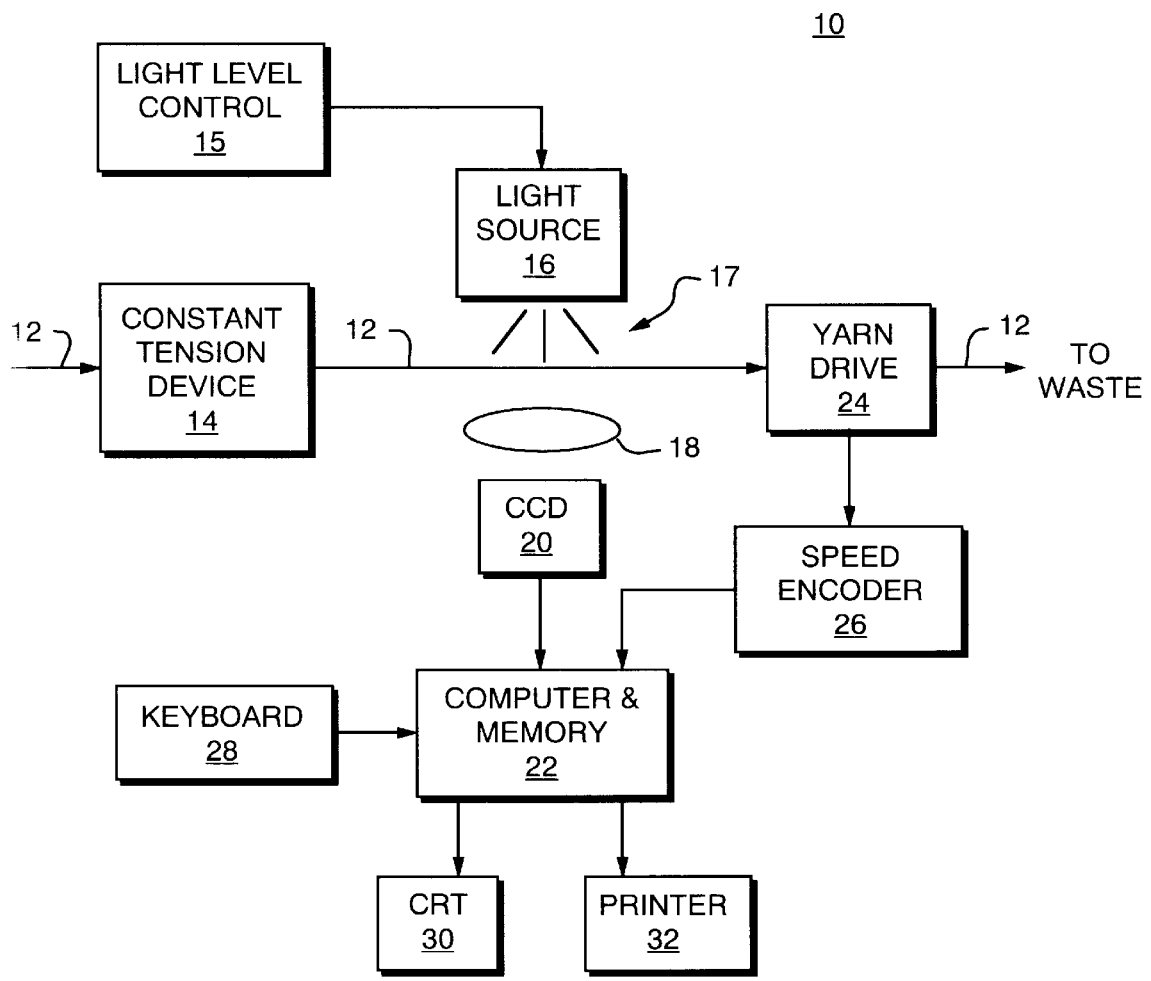
FIG. 1 is a block diagram of a computer-controlled device for determining relative yarn hairiness according to this invention, in which the claimed computer program may reside, and that can be used to practice the methods of this invention.

A schematic block diagram of a computer-controlled device according to this invention for determining relative yarn hairiness, in which the claimed computer program resides, and that can be used to practice the claimed methods of this invention, is shown in FIG. 1. This device is described in U.S. Pat. No. 5,319,578, issued on Jun. 7, 1994, and incorporated herein by reference. A device embodying the yarn drive and imaging capability of FIG. 1, the Yarn Profile Analyzer, is available from Lawson-Hemphill, Inc., of Central Falls, R.I.

Device 10 is used to make width or yarn profile measurements of yarn 12 moved through imaging area 17 by yarn drive 24. Yarn 12 passes through constant tension device 14 before entering imaging area 17 so that it is under a constant, reproducible tension while it is being imaged. This allows device 10 to develop useful, accurate, quantitative data concerning yarn that is measured with the device, independent of any external equipment such as the machinery used to produce the yarn, or any other production equipment.

Light source 16 provides sufficient light in imaging area 17 so that the image focussed by lens 18 onto CCD array 20 is sharp enough for the desired purposes. Light level control 15 may be included to allow operator control of the light output level of light source 16. Light source 16 may be an incandescent lamp, and control 15 may be a regulated DC lamp power supply with variable output. This provides a variable strength but steady light source without 60 Hz flicker. In the preferred embodiment, CCD 20 is a 1" linear CCD array having 2,048 pixels spaced on 13 micron centers. Lens 18 may magnify the image four times so that a ¼" wide yarn fills the entire 1" array.

Encoder 26 is used to measure the lengths of yarn transported by drive mechanism 24. The output of encoder 26 may be translated into yarn lengths, and thus yarn speed, by computer 22. Keyboard 28 is used by the operator to enter commands for operation of computer 22 in a known fashion. The output of computer 22 may be applied to either CRT 30 and/or printer 32 as desired to create a visible output.

Figure 2A:
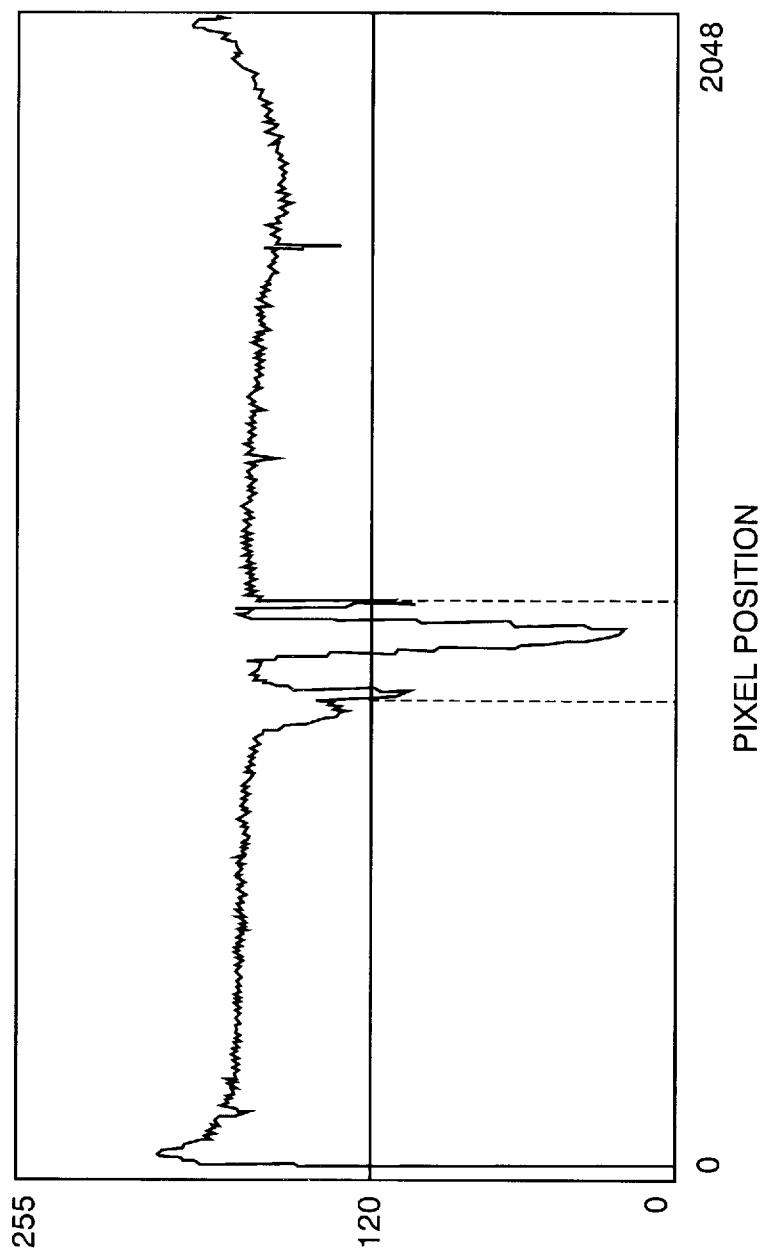
Figure 2C:
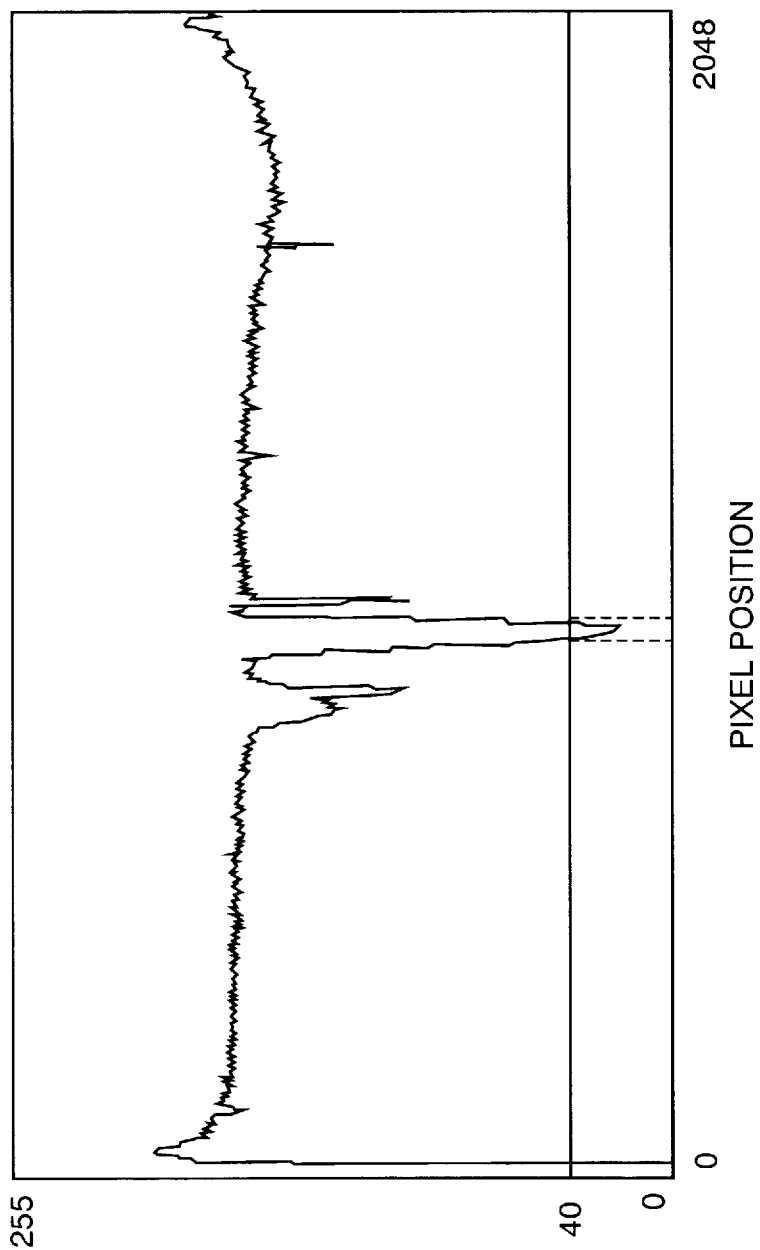
Figure 3:
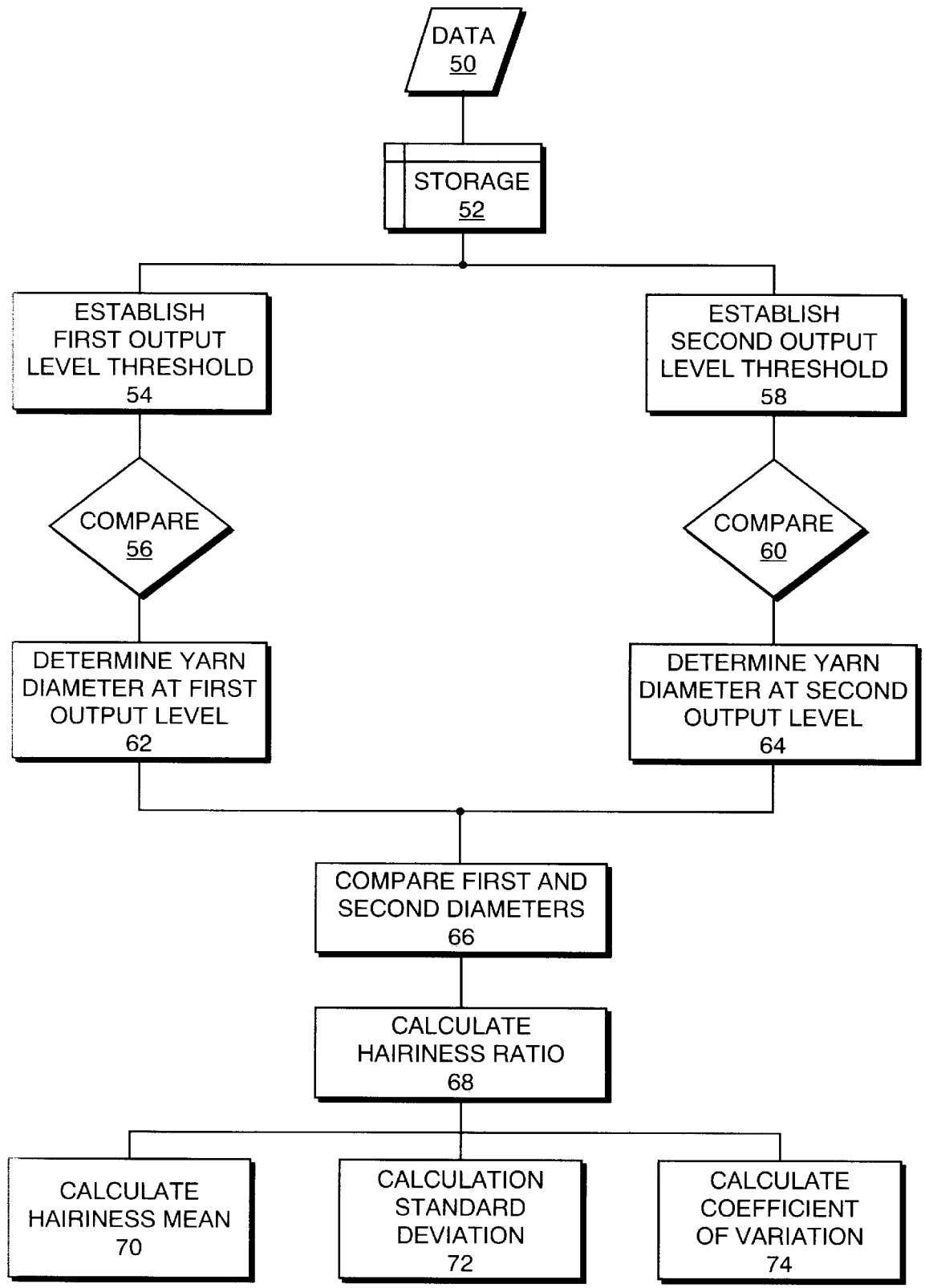
FIG. 3 is a flow diagram of a preferred embodiment of the computer software of the invention.

The amount of light sensed by each pixel of array 20 is provided as a related voltage at the output of array 20. Computer 22 includes in its memory software that allows the operator to establish an adjustable CCD output threshold level, so that device 10 reports a blocked (unlighted) pixel only when a selected amount of the maximum possible incident light is received by the imaging device elements (pixels). In the described embodiment, the output for each element of array 20 is an 8 bit word. Thus, the output levels vary from 0 to 255. The threshold level is selected in steps 54 and 58 as shown in FIG. 3 as a number between 0 and 255, as is more fully set forth below in conjunction with FIGS. 2A through 2C.

Since the pixel output voltage is directly related to the amount of light incident thereon, a high threshold level increases the sensitivity of the elements to relatively few hairs, which causes relatively little blockage of the light received by each element. Lower threshold levels will effectively filter out the hairs to measure the denser yarn core. Threshold levels can be established a priori for a particular yarn to be tested to accomplish a desired test result.

The input from CCD 20 to computer 22, for each image of the yarn captured, is an eight bit word from each of the 2,048 CCD sensing elements. Computer 22 is programmed to determine the diameter of the yarn in step 62 and/or 64 as shown in FIG. 4, by determining the furthest-spaced pair of pixels having an output of at least the chosen threshold value. This determination, and the manner in which it is used in this invention, is better understood with reference to FIGS. 2A through 2C, which are plots of a single yarn image with three different CCD output thresholds applied. Plotted in these graphs is the pixel position (from 1 to 2,048) on the X axis, and the pixel output intensity (from 0 to 255) on the Y axis. As can be seen in FIG. 2A, the pixel outputs are relatively high until the first outer perimeter of yarn hairiness is detected at points 40 and 42. This yarn hairiness begins to partially block pixels, thereby decreasing the pixel output values. The more solid core of the yarn is indicated at point 44 by the relatively narrow band in which the pixel output drops dramatically.

Software residing in the memory of computer 22 is enabled to determine the measured width at the set threshold level as follows. Computer 22 as shown in FIG. 3, sequentially receives the 2,048 pixel output levels of the 2,048 element linear CCD array in step 50. These values are sequentially compared, in step 56 or 60, to the pixel voltage threshold level, established in step 54 or 58, to sequentially determine whether each pixel is considered to be open (value at or above the threshold) or blocked (value below the threshold). The software then determines if the state (open or blocked) of the current pixel is different from that of the previous pixel. If so, there has been a transition from unblocked to blocked, or blocked to unblocked. By determining if the previous pixel voltage was greater than or less than the threshold, the type of transition is determined. The software assembles a word for each transition which represents the pixel position and the direction of that transition. The software then examines, in step 62 or 64, all of these words and determines the pixel position of the first high to low transition, and the pixel position of the last low to high transition. The diameter is then reported as the number of pixels between those two determined positions.

FIG. 2A illustrates a relatively high threshold of 120 which, as can be seen from the plot by line 46, picks up some but not all of the blockage caused by hairiness. When the threshold is dropped to 100 and then to 40 as depicted in FIGS. 2B and 2C by lines 47 and 48, respectively, only the relatively solid core portion of the yarn that blocks substantially all of the light is measured.

The two or more different thresholds can be applied in a number of different manners in step 66. If short sections of yarn are measured, and thus there are a relatively few number of yarn images captured so that each of the 2,048 pixels of each image can be stored in the computer memory, the different thresholds can be applied to this stored data, thus allowing the yarn to be measured only once. In most situations, however, relatively long lengths of yarn will be measured, making storage of the voluminous amounts of data impractical. In this case, one length of yarn from a package can be measured at one threshold, and then a second length measured at a second threshold. Alternatively, a single length of yarn could be routed through the measuring device of FIG. 1 twice. However, the processing of yarn through the device of FIG. 1 can affect the hairiness. Thus, passing yarn twice through the equipment can skew the results. To avoid this, two or more cameras can be placed in the yarn path in series, to make measurements at two or more thresholds on a single pass through of a single length of yarn.

The system, computer program, and method of this invention allow the determination of the true hairiness level of yarn. Also, the core of the yarn alone can be studied. This information can be used as desired in yarn manufacturing and processing operations. For example, the measurement of the hairiness, or the ratio of overall diameter to core diameter, calculated in step 68, which can be called a "hairiness factor", can be used as part of the overall grading of a manufactured yarn. Because the measurement is made automatically and calculated by a computer, the hairiness factor can be used as an input to yarn clearing technology to remove portions of yarn with an unacceptable hairiness factor to improve the overall quality of the yarn package.

As an example of use of this invention, the hairiness factor can be determined on the basis of 20 meters of yarn, by combining 20 test of 1 meter each. This allows the calculation of the average or mean hairiness, and also the standard deviation and coefficient of variation.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A method of determining yarn hairiness of a yarn, comprising:
   measuring the diameter of the yarn as including at least hairs;
   measuring the diameter of the yarn as including fewer hairs; and
   comparing the measured diameters to determine the overall yarn hairiness;
   wherein both of said diameter measurement steps are yarn shadow measurement steps which comprise:
      shining a light on the yarn;
      capturing an image of the yarn shadow with an imaging device having an output level related to the amount of light shining on the imaging device and which comprises a number of separate, closely-spaced light sensing elements, each with an output level;
      establishing sensing element output level indicative of an element being blocked by the yarn from receiving sufficient light; and
      determining the furthest-spaced pair of light sensing elements blocked by the yarn, as indicative of the yarn diameter at the established sensing element output level;
   wherein, measuring the diameter of the yarn as including at least some hairs includes establishing a selected relatively large sensing element output level as indicative that an element is blocked by the yarn, to make the sensing elements more sensitive to yarn hairs.

2. The yarn hairiness determination method of claim 1 in which measuring the diameter of the yarn as including fewer hairs includes establishing a selected relatively low sensing element output level, as indicative that an element is blocked by the yarn to make the sensing elements less sensitive to yarn hairs, for the purpose of determining the yarn core.

3. The yarn hairiness determination method of claim 2 in which the yarn shadow measurement steps are accomplished by a single pass of the yarn across the imaging device.

4. The yarn hairiness determination method of claim 3 in which the imaging device comprises two or more cameras.

5. The yarn hairiness determination method of claim 4 in which the two or more cameras are positioned in series.

6. The method of determining yarn hairiness of a yarn of claim 1, wherein the comparing step to determine the overall yarn hairiness comprises calculating the ratio of the diameter including fewer hairs to the diameter including at least some hairs.

7. A computer program residing in the memory of a computer that is responsive to a yarn profile analyzer device, in which the yarn profile analyzer device includes a light source for shining light on a moving yarn, and an imaging device capturing a shadow image of the moving yarn, the imaging device including a number of separate, closely-spaced light sensing elements, each with an output level related to the amount of light shining on the element, comprising:
   computer program means for establishing a selected relatively large sensing element output level as indicative that an element is blocked by the yarn, to make the sensing elements more sensitive to yarn hairs;
   computer program means for establishing a selected relatively low sensing element output level as indicative that an element is blocked by the yarn, to make the sensing element less sensitive to yarn hairs, for the purpose of determining the yarn core, to assist in distinguishing the yarn core from the yarn hairs; and
   computer program means for determining the yarn hairiness from the established large sensing element output level and the established low sensing element output level.

8. The computer program of claim 7 that is responsive to a yarn profile analyzer device, wherein the computer program means for determining the yarn hairiness calculates the ratio of the established large sensing element output level and to the established low sensing element output level.

9. A computer controlled device for determining relative yarn hairiness, comprising:
   a light source;
   means for moving yarn having a width past the light source to create a yarn shadow;
   an imaging device for capturing the yarn shadow, and including a number of separate, closely-spaced light sensing elements, each with an output level related to the amount of light shining on the element;
   means for establishing a selected sensing element output level as indicative that an element is blocked by the yarn; and
   means for determining and capturing the yarn width of a number of closely-spaced portions of the yarn, at two different selected sensing elements output levels, wherein the width is established by the furthest-spaced pair of blocked sensing elements at each selected sensing output levels, for the purpose of distinguishing the yarn core from the yarn hairs.

10. The computer controlled device for determining relative yarn hairiness of claim 9, further including a means for calculating said yarn hairiness based on a ratio of said yarn widths at two different selected sensing elements output levels.

* * * * *